United States Patent
Sataloff (10) Patent No.: US 9,700,408 B1
(45) Date of Patent: Jul. 11, 2017

(54) THYROPLASTY IMPLANT

(71) Applicant: Robert T. Sataloff, Philadelphia, PA (US)

(72) Inventor: Robert T. Sataloff, Philadelphia, PA (US)

(*) Notice: Subject to any disclaimer, the term of this patent is extended or adjusted under 35 U.S.C. 154(b) by 69 days.

(21) Appl. No.: 14/296,213

(22) Filed: Jun. 4, 2014

(51) Int. Cl.
*A61F 2/12* (2006.01)
*A61F 2/20* (2006.01)

(52) U.S. Cl.
CPC ..................... *A61F 2/20* (2013.01)

(58) Field of Classification Search
CPC ......................................... A61F 2/12
See application file for complete search history.

(56) References Cited

U.S. PATENT DOCUMENTS

| | | | | |
|---|---|---|---|---|
| 5,146,933 A | * | 9/1992 | Boyd | A61B 19/24 128/899 |
| 5,496,370 A | * | 3/1996 | Hamas | A61F 2/0059 623/23.67 |
| 2004/0092948 A1 | * | 5/2004 | Stevens | A61B 10/025 606/96 |
| 2007/0233273 A1 | * | 10/2007 | Connell | A61F 2/12 623/23.72 |
| 2010/0228347 A1 | * | 9/2010 | Schuessler | A61F 2/12 623/8 |

* cited by examiner

*Primary Examiner* — Thomas J Sweet
*Assistant Examiner* — Wade P Schutte
(74) *Attorney, Agent, or Firm* — Andrew L. Salvatore, Esquire (57) ABSTRACT

An adjustable thyroplasty implant comprising at least one inflatable bladder to apply pressure against the vocal folds to adjust vocal medialization easily in the operating room. The implant may contain at least one injection port corresponding with each bladder for injection of a substance into each bladder using a standard syringe. The implant allows for easy adjustment during initial thyroplasty surgery. Further, the implant permits easy adjustment of the implant after surgery by injection or withdraw of the substance within the bladder utilizing a syringe without the need for additional surgery. The implant may contain a means of detecting a means of detecting the injection port post-surgery using x-ray or fluoroscopic examination.

14 Claims, 6 Drawing Sheets

THYROPLASTY IMPLANT

BACKGROUND OF THE INVENTION

Field of Invention

The invention is related to the structure of an implant that can be placed inside the thyroid cartilage of a human or animal larynx (voice box) in order to medialize the vocal folds (vocal cords). The surgical procedure is called a thyroplasty and is well established. It is used to treat vocal fold paresis, vocal fold paralysis, and other conditions that cause glottic insufficiency (failure of the vocal folds to approximate completely) which result in dysphonia (vocal weakness, breathiness, hoarseness and other symptoms). The thyroplasty implant of the subject invention is unique and an improvement over the prior art. The invention may be constructed in various sizes as required to serve its purpose.

Description of Prior Art

A thyroplasty is a surgical technique(s) which changes the human voice by altering single or multiple structures of the larynx. By altering the position and tension of the vocal folds, the procedure may create a stronger sounding voice and alter the tonal output of the vocal folds. A thyroplasty procedure involves placing an implant within or against the vocal folds or surrounding tissue in order to change the tension and positioning of the vocal folds which in turn affects the tonal output of the voice.

Thyroplasty implants of the prior art exist in various forms. The original thyroplasty devices were individually hand carved for each patient out of silastic or a similar material. This approach is still used widely. The second approach was pre-formed thyroplasty implants that do not require carving. They are available in several sizes and are made of various material including silastic and hydroxylapatite. They are also still in use. The third approach was to replace an implanted block with a ribbon of Gore-Tex, placement and contour of which can be adjusted easily during the process of insertion. All thyroplasty implants are inserted into the larynx.

Thyroplasty implants must be adjusted to achieve the desired tonal output. Accordingly, when inserted, the implant may need to be reshaped and cut in order to change the shape and size of the implant. The change in the shape and size of the implant alters the amount of pressure placed upon the vocal folds. Similarly, the pressure may be adjusted by changing the implant with another modified implant of the different size and shape. Even under regular present day methods, implant changes must be accomplished by a surgical procedure.

The implants are also subject to late failure because of displacement or because of changes in the patient's anatomy over time. When thyroplasty revision is necessary (a common occurrence), under present day treatment methods, the revision must be accomplished by returning to the operating room and either modifying the existing device or removing and replacing it. All commonly used existing devices present difficulties in effecting fine adjustments to optimize voice quality intraoperatively. These all require an additional operation if revision is needed, and no existing implants may be adjusted after implantation for "fine tuning" the voice without surgery.

Hoffman, in U.S. Pat. No. 8,613,767, attempts to provide an adjustable laryngeal implant which provides for a displacement member which may be varied in size upon insertion of a liquid or other substance into an interior chamber of the displacement member. The displacement member must be fixed to a mount with is attached to thyroid cartilage to prevent the displacement member from moving out of position. The displacement member is then "adjusted" by filling the displacement member through an inlet port connected to flexible tubing connected to a fluid reservoir. A syringe may be used to fill the fluid reservoir. When proper adjustments have been made, the fluid tubing is cut and the inlet port must be sealed.

However, Hoffman has many disadvantages which render the invention difficult to use, and Hoffman fails to overcome many of the limitations of the prior art. The Hoffman device cannot be maintained indefinitely with flexible tubing attached, and accordingly, the flexible tubing used to fill the bladder must be removed. Future adjustments of the device require additional surgeries. Further, the Hoffman device only contains a single displacement member which fails to provide a sufficient degree of adjustment control. The present invention overcomes the limitations of Hoffman by providing for a device which provides for greater means of adjustment during initial surgery and a means of adjustment post-operatively using minimally invasive techniques. Therefore, it is the object of the present invention to provide a device that can be adjusted easily intraoperatively, and that can be adjusted postoperatively as needed over time, without the need for additional surgery.

SUMMARY OF THE INVENTION

The present invention has been accomplished to provide a device that can be used to adjust vocal medialization easily in the operating room, and that can be adjusted postoperatively outside of the operating room. According to the preferred embodiment of the present invention, a thyroplasty device will be implanted in the usual fashion. However, it will have a thin platform and block to which inflatable bladders are attached. The bladders are shaped to fit the contour of the larynx (larger posteriorly than anteriorly in the preferred embodiment) and can be filled independently through injection ports mounted in the thyroplasty device.

It is the primary object of the present invention to provide a device that permits easy adjustment in the operating room and outside the operating room. In the operating room, the size of the anterior, middle and posterior thirds of the thyroplasty device can be adjusted by filling the bladders with saline or other liquid or substance, using a syringe needle inserted through the injection ports. The injection ports will be similar to that currently approved by the FDA for use in intravenous injection ports (such as those that are used for chemotherapy). The materials used to make the bladder may be similar to those used and approved by the FDA for other saline-inflatable implanted devices such as breast implants and penile implants. Thyroplasty procedures usually are performed under local anesthesia with sedation, so the voice can be tested; but they can be performed under general anesthesia.

Adjustments in the device proposed herein can be made easily and instantaneously intraoperatively by adjusting the amount of saline in each bladder using a syringe. Adjustments can also be made postoperatively by adjusting the amount of liquid in each bladder under fluoroscopic or other guidance. Each of the three injection ports may be partially radiopaque and marked by varying shapes or other means. Consequently, if adjustments need to be made at any time following surgery, the amount of saline or other substance in each of the three bladders can be adjusted by adding more saline or removing saline simply be accessing the injection ports with a needle placed through the skin of the neck (after sterile preparation) using fluoroscopic or other guidance.

This implant may also be made available in various sizes and with varying numbers of bladders (more or less than three).

The invention overcomes the limitations of the prior art in which it is more difficult to adjust the size and positioning of a thyroplasty implant during surgery. Further, additional modifications to prior art implants require additional surgery. Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE INVENTION

The thyroplasty implant 10 of the present invention is used to apply pressure against vocal folds and surrounding tissue in the larynx in order to modulate the vibrations of the vocal folds (vocal cords) 100. Thyroplasty procedures are often used to improve voice quality where an individual's voice is weak due to positioning of the vocal folds at a distance from each other causing the vocal folds to vibrate ineffectively. The larynx is surrounded by cartilage and the vocal folds are positioned over the trachea 120 from the anterior position to the posterior position and attached at each end to surrounding cartilage.

The thyroplasty implant 10 of the subject invention comprises a series of inflatable bladders 30 which may be adjusted in order to apply varying amounts of pressure against the vocal folds. In a preferred embodiment, three bladders may be used, but the number of bladders may be varied as required or desired. Each of the bladders may be constructed of a silastic or a similar substance forming a bladder wall 33 to permit flexibility and expansion of the bladders. Each of the bladders defines a chamber 35 within the interior of the bladder to receive a substance, such as saline solution, to fill the interior of the bladder and alter the size of the bladder. Each bladder contains an opening 37 to permit the injection of saline or other substance into the bladder. As shown in FIGS. 1-8 and 11, the bladders may be positioned on a platform 20 which is attached to a block 95. The block 95 acts not only to secure the bladders but also to anchor the structure within the thyroid cartilage 110. Preferably, the platform is relatively thin and pliable and the block should be thick enough to securely position the implant with the thyroid cartilage.

The size of the bladders may be varied by filling the bladders with a liquid solution or other substance. Preferably, a saline solution will be used to fill the bladders to a desired size to apply appropriate pressure against the vocal folds and surrounding tissue. The bladders may be filled by injecting a solution through injection ports 40 associated with each bladder. A syringe 80 may be used to inject the solution into the ports, and ports may be interiorly sized to receive the needle of a standard syringe. Syringes and the use of syringes are well known in the medical field and the art. The injection ports should contain a means to prevent the backflow of solution. For example, the ports may contain a rubberized material which returns to a closed position after injection and acts as a check valve. A separate check valve may also be used.

Figure 1:
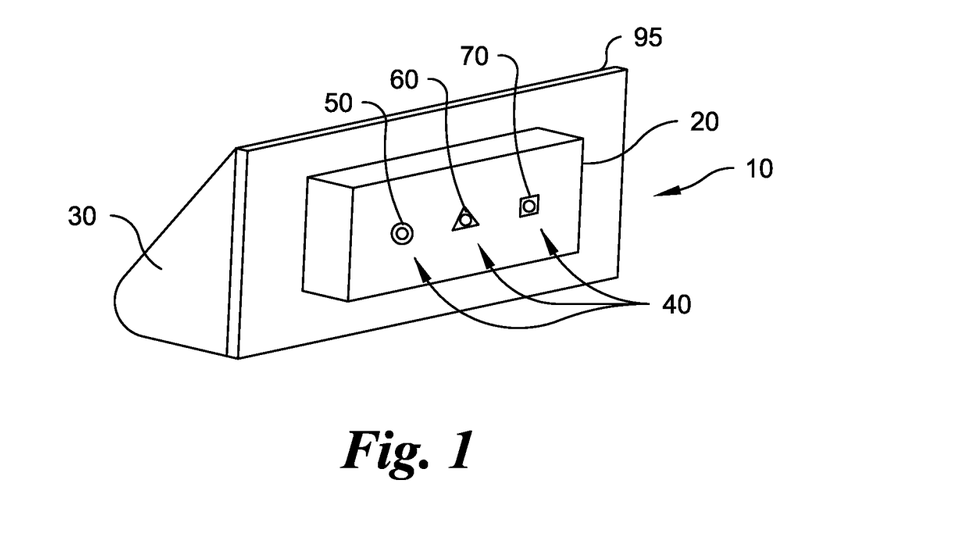
FIG. 1 shows a perspective view of a thyroplasty implant according to the invention.
Figure 2:
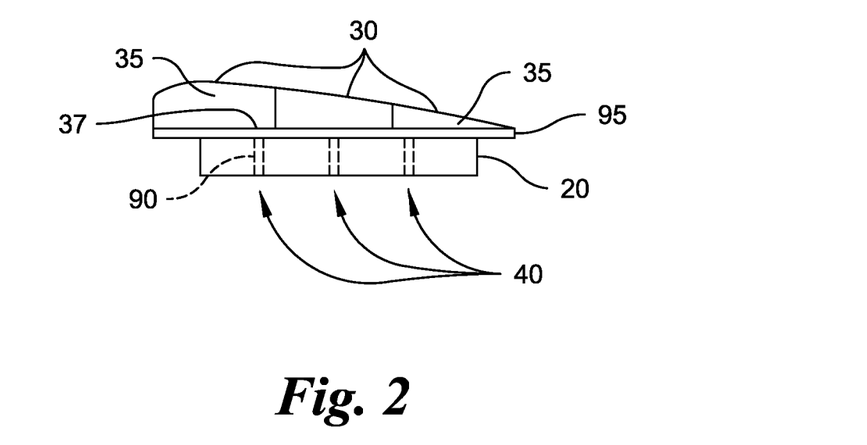
FIG. 2 shows a top plan view of a thyroplasty implant with bladders not inflated according to the invention.
Figure 3:
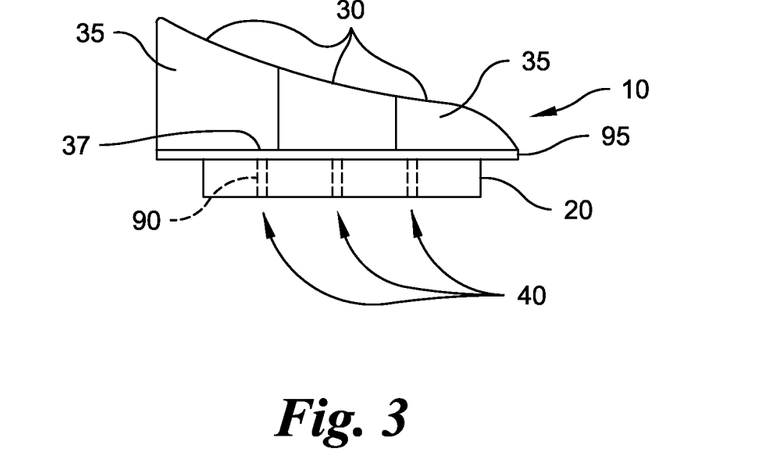
FIG. 3 shows a top plan view of a thyroplasty implant with all bladders fully inflated according to the invention.
Figure 4:
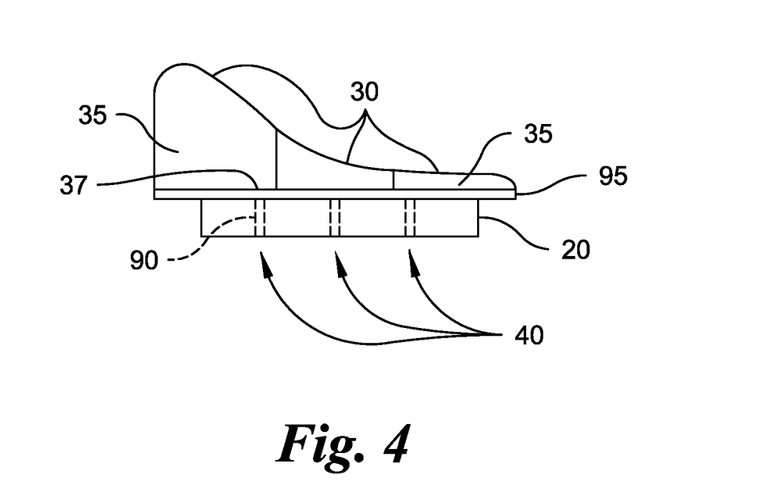
FIG. 4 shows a top plan view of a thyroplasty implant with each of the bladders inflated to varying degrees according to the invention.
Figure 7:
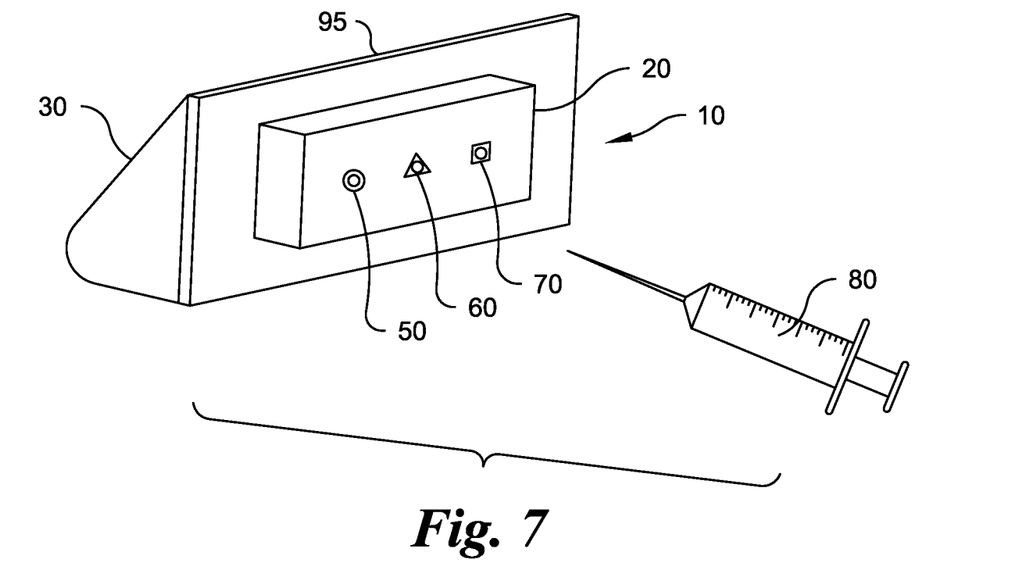
FIG. 7 shows a perspective view of a thyroplasty implant with syringe to insert substance to inflate bladders according to the invention.
Figure 8:
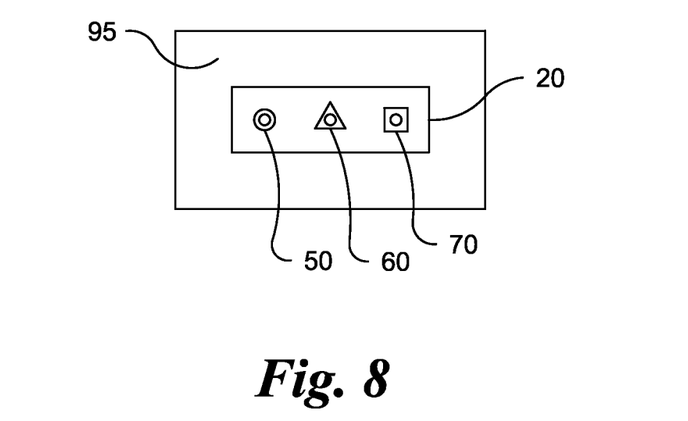
FIG. 8 shows a front elevational view of a thyroplasty implant according to the invention.

The ports may each contain identifying shapes so that a particular port may be identified under x-ray analysis. By way of example, as shown in FIGS. 1, 7, and 8, a circular port 50 may contain a circular metallic exterior perimeter, a triangular port 60 may contain a triangular metallic exterior perimeter, and a square port 70 may contain a square metallic exterior perimeter. Alternatively or in addition, the ports may contain specific radiopaque markings to identify each port individually. Accordingly, even after a surgical procedure, the individual ports may be identified under x-ray or fluoroscopically to identify the specific location of each port without the need for additional surgery.

The ports may be connected to the bladders through ducts 90 (identified as dashed lines) which run through the platform, through the block, and connect each port with its respective bladder. In this manner, each bladder may be filled individually to a desired amount so that the correct amount of pressure is exerted against the vocal folds.

Figure 9:
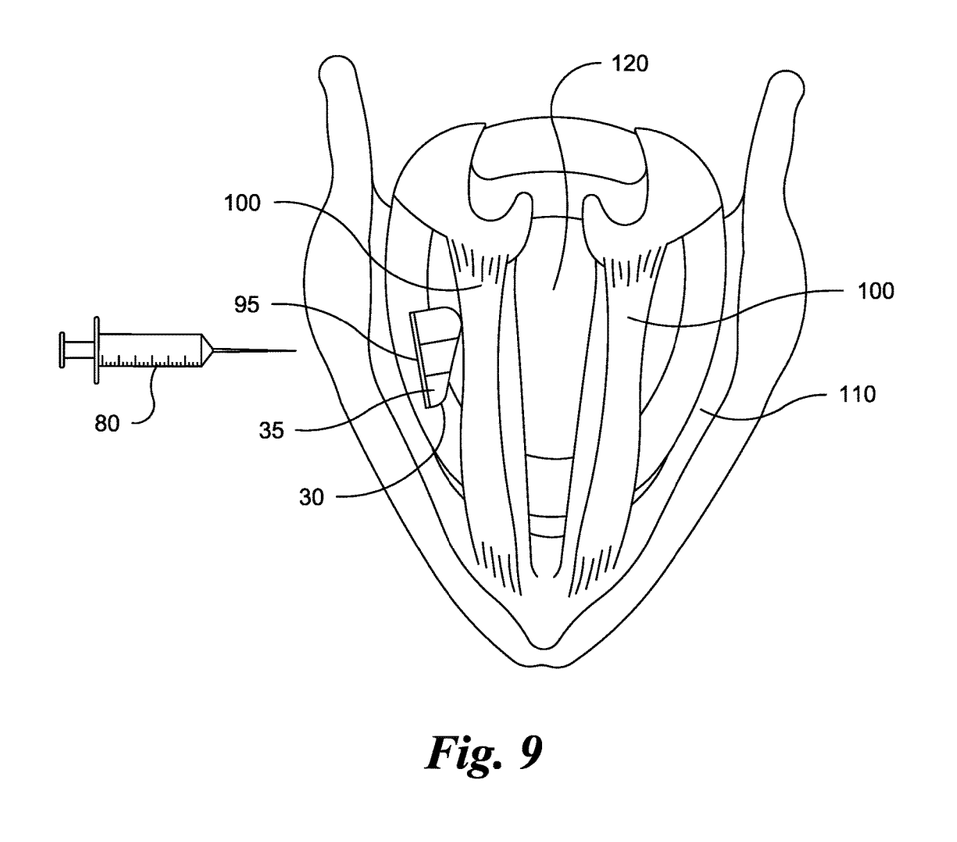
FIG. 9 shows a top plan view of the human anatomy in the area of the larynx with top plan view of thyroplasty implant in position and syringe for inflation of bladders according to the invention.

In a thyroplasty surgical procedure, an incision is made in the thyroid cartilage 110 in the neck and the implant inserted through the incisional opening to apply pressure to the vocal folds and surrounding tissue. As shown in FIG. 9, the bladders are positioned against the tissues of the vocal folds to move vocal folds in position closer in proximity to each other. As each bladder may be sized independently, more or less pressure may be placed against the vocal folds anteriorly or posteriorly as required to achieve optimum desired voice quality. In the example shown in FIG. 9, the bladder position most posterior in the larynx is inflated to a larger size to apply more pressure against the vocal fold in this region. The syringe may be used to inject a substance into each bladder independently.

Figure 5:
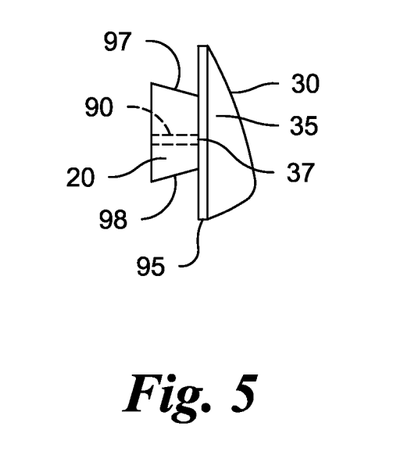
FIG. 5 shows a side elevational view of a thyroplasty implant with bladders not inflated according to the invention.
Figure 6:
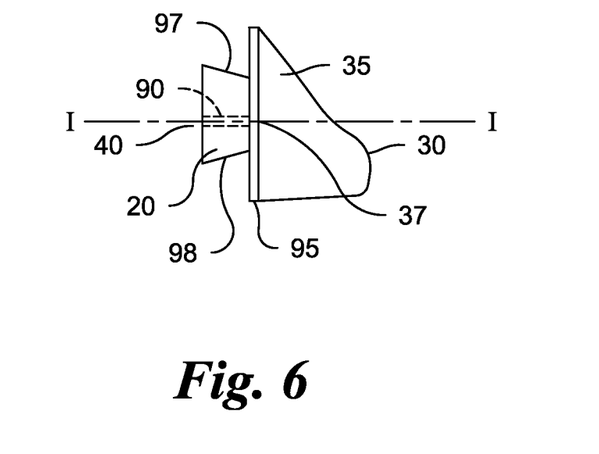
FIG. 6 shows a side elevational view of a thyroplasty implant with bladders inflated according to the invention.
Figure 10:
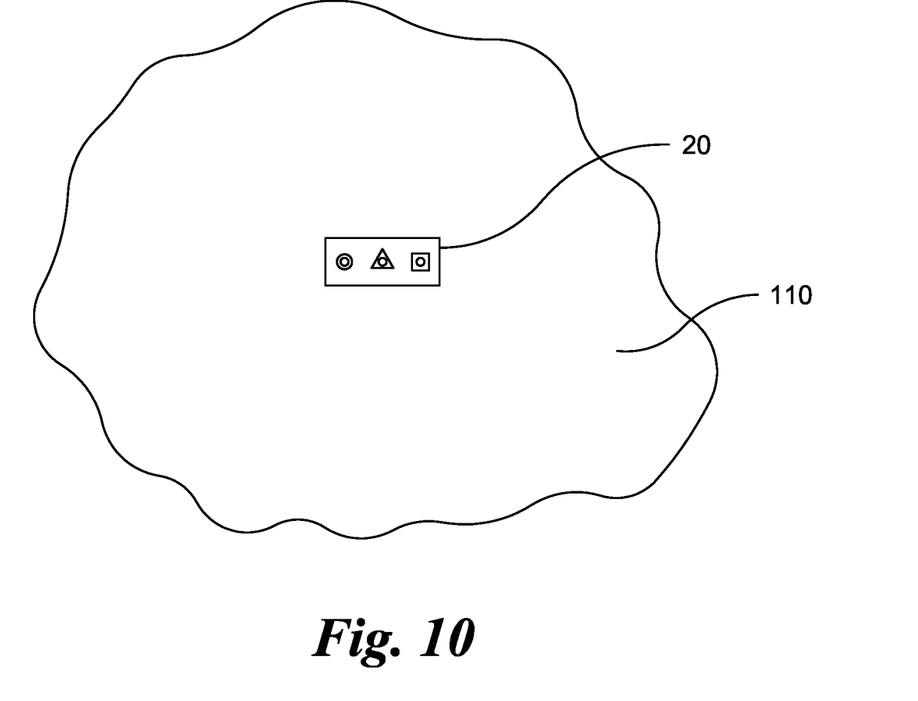
FIG. 10 shows a side elevational view of human anatomy in the area of the larynx with front elevational view of thyroplasty implant in position according to the invention.
Figure 11:
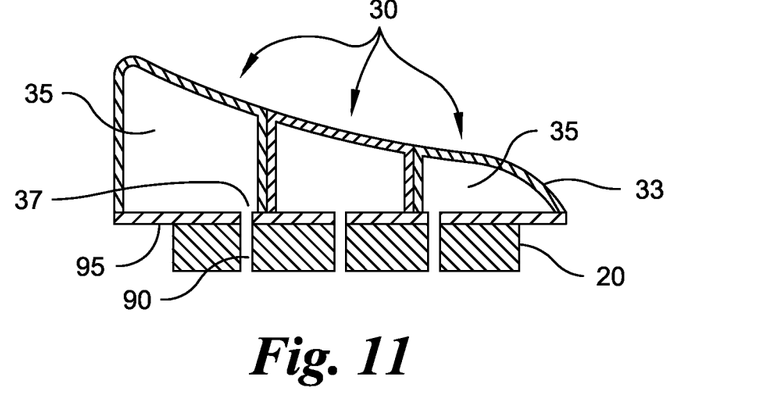
FIG. 11 shows a cross sectional view of a thyroplasty implant taken at line I as shown in FIG. 6 according to the invention.

FIG. 10 depicts the device inserted through the thyroid cartilage 110 in the side of an individual's neck in the region of the larynx. An incision is made through the thyroid cartilage and the block 95 is sized to fit securely within the incisional opening. This block stabilizes the implant and, as shown in FIGS. 5 and 6, an upper ridge 97 and a lower ridge 98 on the block may be constructed to angle inwardly toward the bladders such that the block fits securely within the incisional opening in the thyroid cartilage (a lock and key configuration).

As noted previously, a thyroplasty procedure is usually performed under local anesthesia with sedation. Bladders may be easily filled to desired amounts during surgery as noted. However, during and as a result of surgery, the affected individual often experiences swelling. Accordingly, even though a desired voice quality may be achieved during the surgical procedure, once swelling goes down after surgery, the voice quality may change. Typically, under existing thyroplasty procedures, a second surgery may become necessary to further adjust the implant due to the change in tissue structure.

The subject thyroplasty implant obviates the need for additional surgery. If a reduction in swelling or another change in the anatomy of the affected individual causes voice quality to change, the size of the bladders may be adjusted simply by inserting the syringe (after appropriate sterilization techniques) into the neck and into the desired injection port of the implant. X-ray analysis may be used to detect the specific port shape, e.g. the circular port, the triangular port, or the square port, and the syringe (also visible under x-ray) may be directed toward the appropriate port. Similarly, specific radiopaque markings may be used to guide the syringe toward the appropriate port under fluoroscopic examination. Solution may then be injected into the bladders until the bladders are inflated to the desired amount and the desired voice quality is achieved. This procedure is more effective than present techniques as the procedure is minimally invasive, and the individual will experience little or no swelling during any subsequent "adjustment" procedure.

The invention has been disclosed in terms of preferred embodiments which fulfill all of the objects of the present invention and overcome the limitations of the prior art. It will be understood that each of the elements described above, or two or more together, may also find useful application of other types or methods differing from the types described above. Various changes, modifications, and alterations from the teachings of the present invention may be contemplated by those skilled in the art without departing from the intended spirit and scope thereof. It is intended that the present invention only be limited by the terms of the appended claims.

I claim:

1. A thyroplasty implant comprising:
   At least one inflatable bladder, each bladder containing a bladder wall which defines a sealed chamber within the interior of the bladder and each bladder wall being the outermost layer of each bladder, each bladder defining an opening to receive a substance into the chamber to inflate the bladder, each bladder operating independently of other the bladders and each being expandable to various sizes independently of the other bladders, and each bladder wall being configured to come into contact with vocal folds,
   An anchoring block connected to at least one inflatable bladder at one end of the bladder configured to anchor the implant into cartilage, the block having at least one duct passing through the block, each duct corresponding with a bladder, the duct providing a passageway into the opening in the bladder,
   A platform connected to the block, the platform having at least one injection port passing through the platform, each port corresponding to a duct to provide a passageway into the duct and into the bladder.

2. A thyroplasty implant as set forth in claim 1 wherein each bladder wall is constructed of a silastic substance and wherein the bladder wall is flexible and expandable.

3. A thyroplasty implant as set forth in claim 1 wherein each port is sized to receive a needle of a standard syringe.

4. A thyroplasty implant as set forth in claim 1 wherein each injection port contains a means to prevent the backflow of the substance used to inflate the bladder.

5. A thyroplasty implant as set forth in claim 4 wherein the means to prevent the backflow of the substance comprises a rubberized material positioned within each port.

6. A thyroplasty implant as set forth in claim 4 wherein the means to prevent the backflow of the substance comprises a check valve.

7. A thyroplasty implant as set forth in claim 1 wherein each port is constructed of a metallic material capable of detection under x-ray analysis.

8. A thyroplasty implant as set forth in claim 7 wherein each port defines an interior circular passageway sized to receive a needle of a standard syringe and wherein an exterior portion of each port defines at least one shape distinguishable from other ports.

9. A thyroplasty implant as set forth in claim 8 wherein each shape is selected from the group consisting of a circle, a triangle, and a square.

10. A thyroplasty implant as set forth in claim 1 wherein each port contains radiopaque markings capable of fluoroscopic detection.

11. A thyroplasty implant as set forth in claim 1 wherein the block contains an upper ridge and a lower ridge, the upper ridge and the lower ridge being constructed at an angle inwardly toward each other in the direction of the bladders.

12. A method of conducting a thyroplasty utilizing the thyroplasty implant of claim 1 comprising the steps of:
   Making an incision in the neck of an individual in the area of the larynx,
   Making an incision in the thyroid cartilage of the individual, the incision in the thyroid cartilage being sized to receive the block of the thyroplasty implant of claim 1 such that the block fits securely within the incisional opening,
   Inserting the thyroplasty implant of claim 1 through the incisional opening in the thyroid cartilage, at least one bladder of the thyroplasty implant being positioned at or against the vocals folds of the individual,
   Inserting a needle of a standard syringe into at least one port of the thyroplasty implant of claim 1, the syringe containing a substance to fill the bladder of the thyroplasty implant,
   Depressing the syringe to inject the substance into the bladder of the thyroplasty implant until the bladder inflates to a proper level and subsequently withdrawing the needle from the port, and
   Closing incision.

13. A method of conducting a thyroplasty as set forth in claim 12 further comprising the steps of:
   Monitoring the individual to ensure optimum voice quality,
   Utilizing x-ray analysis to detect the location of at least one port in the thyroplasty implant of claim 8,
   Inserting the needle of a standard syringe into the neck of the individual and inserting it into at least one port of the thyroplasty implant, the syringe containing a substance to fill the bladder of the thyroplasty implant,
   Depressing or undepressing the syringe to inject or withdraw the substance into or from the bladder of the thyroplasty implant until the bladder inflates to a proper level and subsequently withdrawing the needle from the port, and Withdrawing the needle from the thyroplasty implant and the neck of the individual.

14. A method of conducting a thyroplasty as set forth in claim 12 further comprising the steps of:

Monitoring the individual to ensure optimum voice quality,

Utilizing fluoroscopic analysis to detect the location of at least one port in the thyroplasty implant of claim 10, Inserting the needle of a standard syringe into the neck of the individual and inserting it into at least one port of the thyroplasty implant, the syringe containing a substance to fill the bladder of the thyroplasty implant, Depressing or undepressing the syringe to inject or withdraw the substance into or from the bladder of the thyroplasty implant until the bladder inflates to a proper level and subsequently withdrawing the needle from the port, and Withdrawing the needle from the thyroplasty implant and the neck of the individual.

\* \* \* \* \*